United States Patent
Galasso

[19]

[11] Patent Number: 5,945,610
[45] Date of Patent: Aug. 31, 1999

[54] APPARATUS FOR DETECTING AND DISPLAYING PRESSURES OF THE FOOT-SOLE AT A STANDSTILL AND DURING MOVEMENT

[76] Inventor: Piero Galasso, Via Nicola Stenone, 65, I-00139 Rome, Italy

[21] Appl. No.: 08/894,432

[22] PCT Filed: Dec. 18, 1996

[86] PCT No.: PCT/IT96/00255

§ 371 Date: Oct. 9, 1997

§ 102(e) Date: Oct. 9, 1997

[87] PCT Pub. No.: WO97/23769

PCT Pub. Date: Jul. 3, 1997

[30] Foreign Application Priority Data

Dec. 21, 1995 [IT] Italy ............................ RM950274 U

[51] Int. Cl.⁶ .................................................... G01D 7/00
[52] U.S. Cl. ..................................... 73/862.042; 356/376
[58] Field of Search ...................... 73/862.046, 862.041, 73/862.042, 862.043, 865.4, 714; 356/376; 128/186.1

[56] References Cited

U.S. PATENT DOCUMENTS

| | | | |
|---|---|---|---|
| 4,640,137 | 2/1987 | Trull et al. ............................ | 73/862.04 |
| 4,843,891 | 7/1989 | Brunner et al. ...................... | 73/862.04 |
| 4,934,197 | 6/1990 | Nitsche .............................. | 73/862.041 |
| 5,128,880 | 7/1992 | White ..................................... | 364/550 |
| 5,134,999 | 8/1992 | Osipov .............................. | 128/661.03 |
| 5,150,902 | 9/1992 | Heisler ................................ | 273/186.1 |
| 5,186,062 | 2/1993 | Roost .................................... | 73/865.4 |
| 5,221,088 | 6/1993 | McTeigue et al. .................. | 273/187.2 |
| 5,230,249 | 7/1993 | Sasaki et al. ............................ | 73/714 |
| 5,361,133 | 11/1994 | Brown et al. .......................... | 356/376 |
| 5,503,029 | 4/1996 | Tamori .............................. | 73/862.046 |
| 5,790,256 | 8/1998 | Brown et al. .......................... | 356/376 |

*Primary Examiner*—George Dombroske
*Assistant Examiner*—Jewel Thompson
*Attorney, Agent, or Firm*—Browdy and Neimark

[57] ABSTRACT

The present invention relates to an apparatus for detecting and displaying pressures of the foot-sole at a standstill and during movement, comprising an elongated modular platform (1) consisting of a multiplicity of footboards with foot-sole sensors (1a, 1b, 1c), having an array of sensors, a control processor (2) connected to the platform (1) by means of an interface board (3), said interface board (3) including a digital/analog converter module (5) connected at its input to the control processor (2) and at its output to each footboard (1a, 1b, 1c), a timing and enable module (6) connected at its input to the control processor (2) and at its output to each footboard (1a, 1b, 1c), and concentrator/switching module (8) having a number of inputs equivalent to the number of footboards (1a, 1b, 1c) and having an output connected to an analog-digital converter module (9) connected at its output to the control processor (2).

3 Claims, 3 Drawing Sheets

APPARATUS FOR DETECTING AND DISPLAYING PRESSURES OF THE FOOT-SOLE AT A STANDSTILL AND DURING MOVEMENT

CROSS-REFERENCE TO RELATED TO U.S. APPLICATION

1. Technical Field

The present invention relates to an apparatus for detecting and displaying pressures of the foot-sole at a standstill and during movement. In particular, this apparatus is designed for the study, at any one moment, of the different postures assumed in the erect position or during a sporting movement, when resting on both feet or on one foot.

2. Background Art

French Patent Nos. 2,273,257 and 2,330,996 disclose a footboard comprising an array of foot-sole sensors located underneath a layer of flexible and electrically conductive material and making contact therewith. Each sensor has a first terminal, kept at a constant predetermined d.c. voltage, and a second terminal, receiving the current which passes through the conductive layer and is modified following the variation in electrical resistance depending on the state of deformation thereof, acting as detector of the foot-sole pressure. The response of the detectors is switched to a single read device via a pyramid of analog multiplexers. The management of these multiplexers is controlled by a set of decoder counters which are governed by a control processor.

The drawbacks of the above embodiments relate not to the operating principle, but more to the dimensional limits of the footboard for measuring the foot-sole pressures. These limits are due to the size of the printed circuits necessary for the array of sensors, said printed circuits not being able to undergo excessive miniaturization. Therefore, a single footboard with the dimensions of a square having a side 32 cm long—dimensions which are currently possible—represents a considerable limitation when performing the tests for measuring the foot-sole pressure, especially during postural graphic measurements and dynamic analyses. In fact, it allows one to perform dynamic measurements which are undoubtedly of limited use from a physiological point of view since they in fact represent a patient who is moving on a same square footboard without performing any consecutive forward steps. Static measurements on a single square foot-board are also unsatisfactory, because the footboard proves to be uncomfortable for patients with pathological conditions, since stiffening of the muscles may occur, thereby falsifying the results of the tests.

SUMMARY OF THE INVENTION

The object of the present invention is therefore that of eliminating the drawbacks mentioned above. The invention, as characterized by the claims which follow, solves the problem of providing an apparatus for detecting and displaying pressures of the foot-sole at a standstill and during movement, which uses in a footboard an array of foot-sole sensors located underneath a layer of flexible and electrically conductive material and making contact therewith, each sensor having a first terminal, kept at a constant predetermined d.c. voltage, and a second terminal, receiving the current which passes through the conductive layer and is modified following variation in the electrical resistance depending on the state of deformation thereof, acting as a detector of the foot-sole pressure, which from a general point of view is characterized in that it comprises an elongated modular platform consisting of a multiplicity of said footboards placed in a cascade arrangement and connected to one another in a direction unidirectionally; each footboard comprising its own array of foot-sole sensors operating at the same voltage and the arrays of foot-sole sensors of all the footboards operating at the same voltage; a control processor connected to said elongated modular platform by means of an interface board; said interface board including: a digital-analog converter module connected at its input to the control processor and at its output to each footboard, a timing and enable module connected at its input to the control processor and at its output to each footboard, a concentrator/switching module, having a number of inputs equivalent to the number of footboards and having an output connected to an analog-digital converter module connected at its output to the control processor; said control processor being provided with suitable software for processing the data received from said sensors, in order to display the static, postural and dynamic measurements of the foot-sole pressures.

BRIEF DESCRIPTION OF THE DRAWINGS

Further characteristic features and advantages of the present invention will emerge more clearly from the detailed description which follows, of a preferred embodiment illustrated purely by way of a non-limiting example in the accompanying drawings, in which.

DETAILED DESCRIPTION OF THE INVENTION

Figure 1:
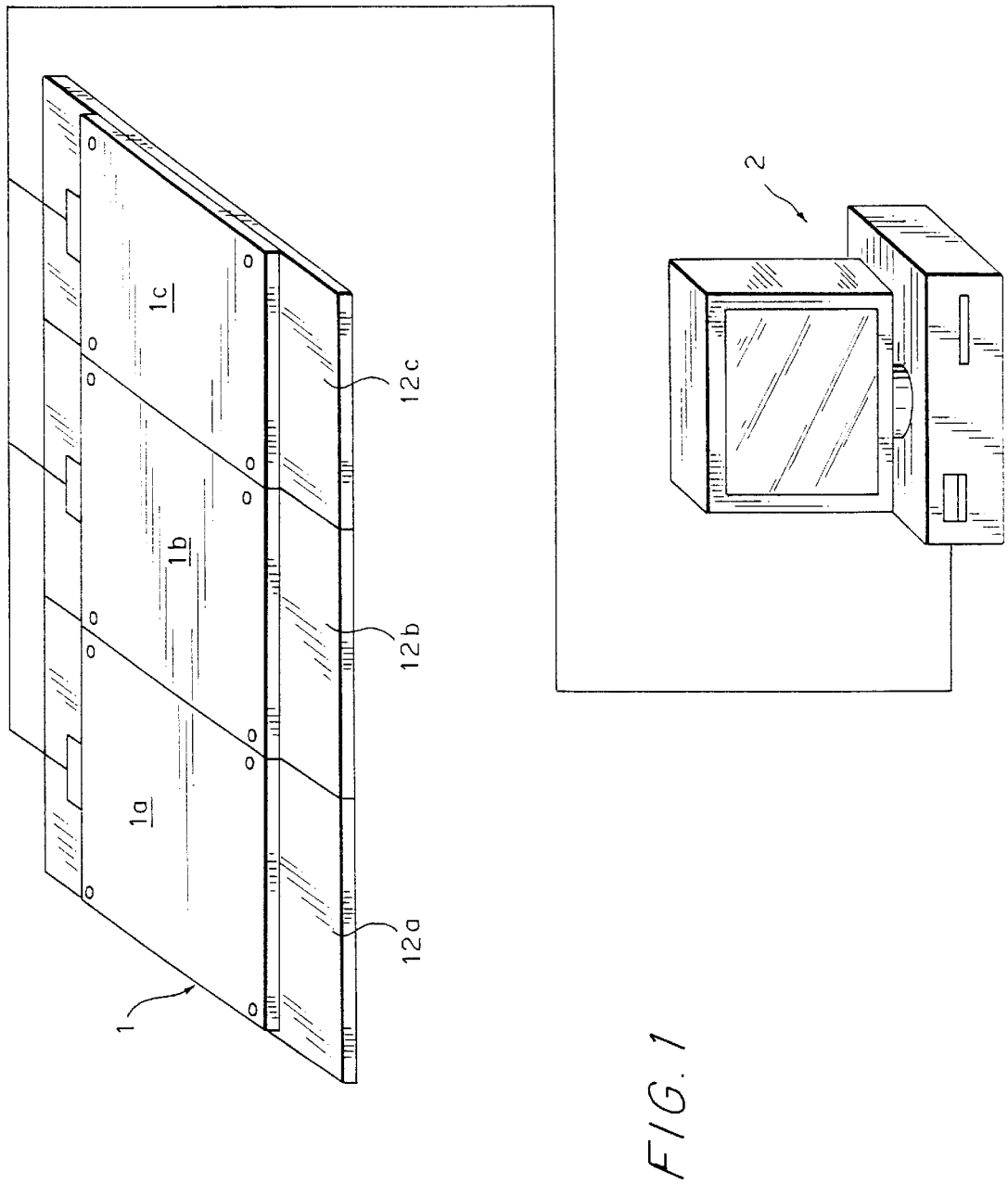
FIG. 1 shows a schematic axonometric view of the apparatus for detecting and displaying the foot-sole pressures according to the present invention.

In accordance with the present invention, in FIG. 1 an apparatus for detecting and displaying pressures of the foot-sole at a standstill and during movement is indicated by 1.

Figure 2:
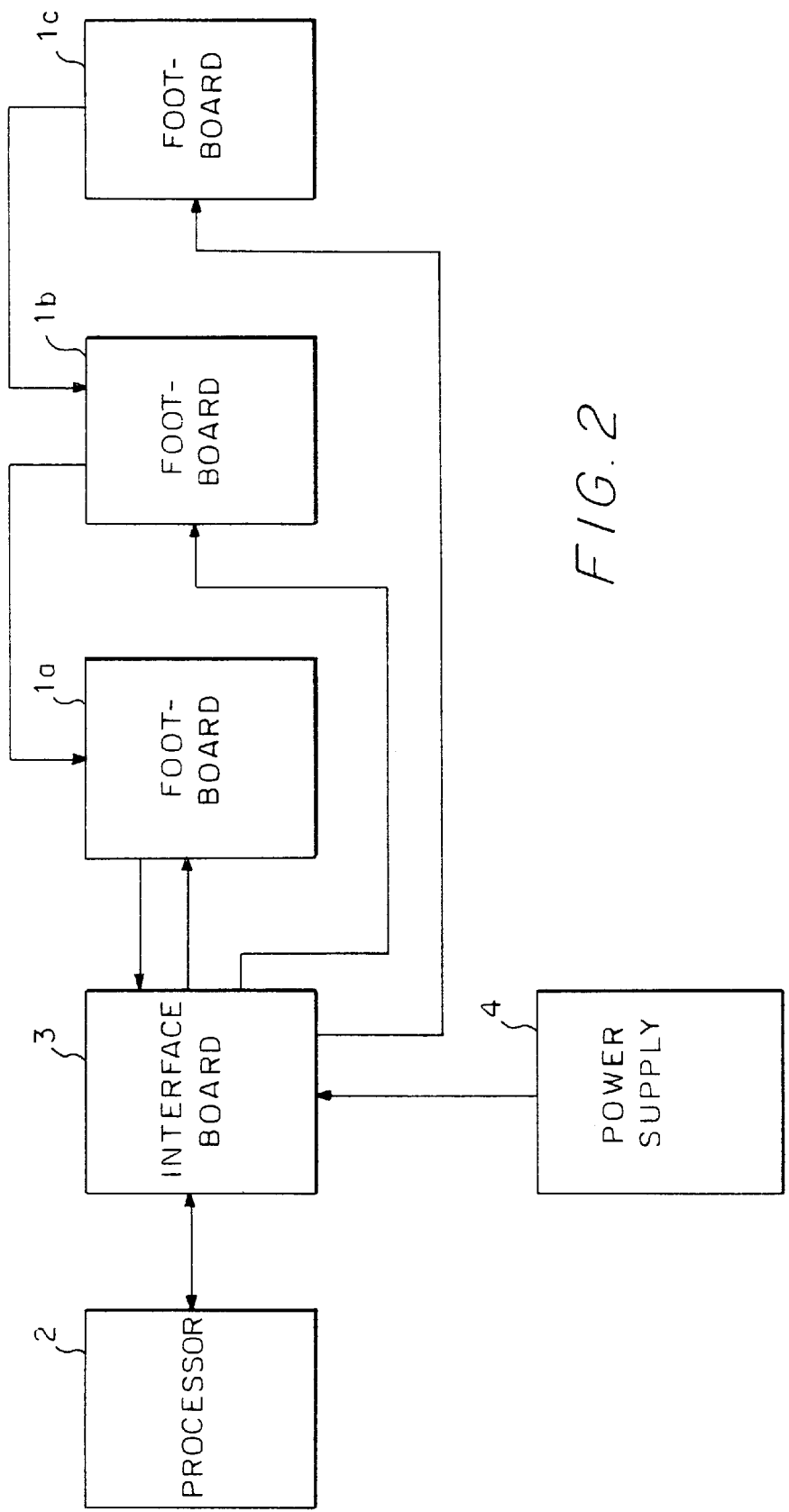
FIG. 2 shows the apparatus according to the invention in the form of a block diagram.

In particular, this apparatus comprises an elongated modular platform 1 which consists of a multiplicity of footboards 1a, 1b, 1c placed in a cascade arrangement and connected to one another, as shown in FIG. 1, in a unidirectional manner. 2 denotes a control processor connected to the elongated platform 1 by means of an interface board 3 (FIG. 2).

Each footboard comprises an array of foot-sole sensors of the known type (and therefore not shown), all operating at the same voltage. These sensors are located underneath a layer of flexible and electrically conductive material and in contact therewith. Each sensor has a first terminal, kept at a constant predetermined d.c. voltage, and a second terminal, receiving the current which passes through the conductive layer and is modified following the variation in electrical resistance depending on the state of deformation thereof, acting as a detector of the foot-sole pressure.

The sensors are connected to the electronic component of each footboard formed laterally with respect to each footboard and indicated by 12a, 12b, 12c in FIG. 1.

The footboards of the modular platform 1 shown are three in number, but may be of a greater number, even though this is not necessary for most of the tests to be performed on the patients.

Figure 3:
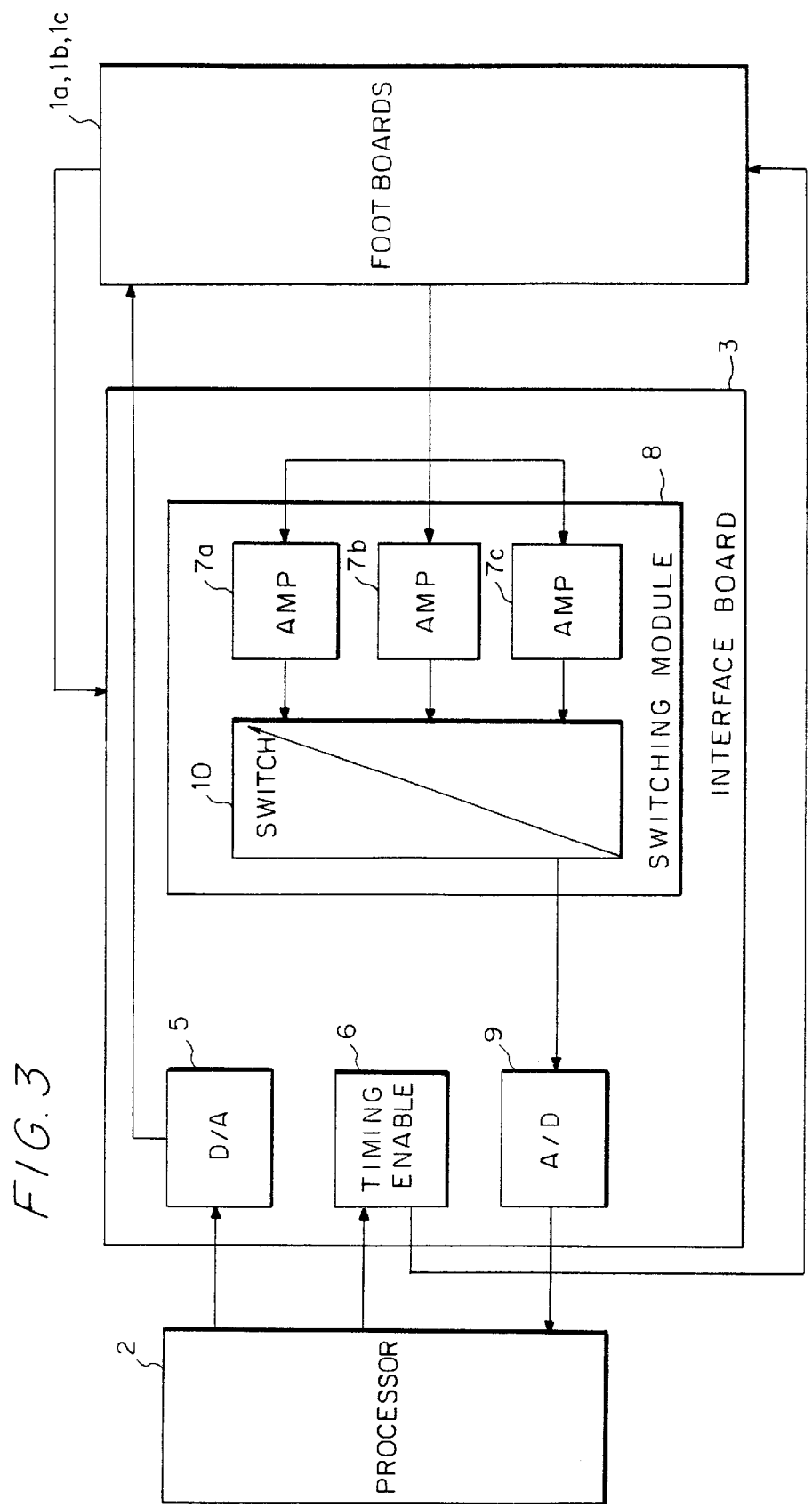
FIG. 3 shows an interface board according to the invention in the form of a block diagram.

FIG. 3 shows the interface board 3 which comprises a digital-analog converter module 5 connected at its input to the control processor 2, while its output is connected respectively to the footboards 1*a*, 1*b*, 1*c*.

The board 3 comprises moreover a timing and enable module 6 connected at its input to the control processor 2 and at its output respectively to each footboard 1*a*, 1*b*, 1*c*. The board 3 is completed by a concentrator/switching module 8 which is connected at its input respectively to each footboard, while the single output is connected to the analog-digital converter module 9. The concentrator/switching module 8 comprises three amplifiers 7*a*, 7*b*, 7*c*, each intended to receive detection of the voltage of the respective footboard, and an electronic switch connected at its input to the three outputs of the amplifiers 7*a*, 7*b*, 7*c* and having the single output, as already mentioned, connected to the analog-digital module 9.

This switch 10 performs continuous scan-reading of the voltage from the footboards 1*a*, 1*b*, 1*c*.

Advantageously, as shown in FIG. 3, an external d.c. power supply 4 is connected to each footboard 1*a*, 1*b* and 1*c*, via the interface board in the case where one does not wish to draw on the internal power supply of the control processor 2.

The control processor 2 is equipped with suitable software for processing the data received from the sensors, in order to display the static, postural and dynamic measurements for consecutive steps of the foot-sole pressures.

In practice, the patient is made to stand on the platform 1, resting on both feet, in order to acquire the orthostatic imprint and is then made to walk in order to acquire the dynamic imprint. The pressure exerted by the foot on each sensor of each footboard provides a set of results which allows one to determine the difference in pressure of each point of contact of the foot both at a standstill and during normal walking in real time.

The invention thus conceived may be subject to numerous modifications and variations, all of which falling within the scope of the same innovative idea. Moreover, all the details may be replaced by technically equivalent elements.

In practice, obviously, modifications and/or improvements are possible, provided that they fall within the scope of the following claims.

What is claimed is:

1. Apparatus for detecting and displaying pressures of the foot-sole at a standstill and during movement, using a footboard with an array of foot-sole sensors located underneath a layer of flexible and electrically conductive material and making contact therewith, each sensor having a first terminal, kept at a constant predetermined d.c. voltage, and a second terminal, receiving the current which passes through the conductive layer and is modified following the variation in electrical resistance depending on the state of deformation thereof, acting as a detector of the foot-sole pressure, characterized in that it comprises:

an elongated modular platform 1 consisting of a multiplicity of said footboards (1*a*, 1*b*, 1*c*) placed in a cascade arrangement and connected to one another in a direction unidirectionally; each footboard comprising its own array of foot-sole sensors operating at the same voltage and the arrays of foot-sole sensors of all the footboards (1*a*, 1*b*, 1*c*) operating at the same voltage;

a control processor 2 connected to said elongated modular platform 1 by means of an interface board 3;

said interface board 3 including:
a digital-analog converter module 5 connected at its input to the control processor 2 and at its output to each footboard (1*a*, 1*b*, 1*c*), a timing and enable module 6 connected at its input to the control processor 2 and at its output to each footboard (1*a*, 1*b*, 1*c*), a concentrator/switching module 8, having a number of inputs equivalent to the number of footboards (1*a*, 1*b*, 1*c*) and having an output connected to an analog-digital converter module 9 connected at its output to the control processor 2; said control processor 2 being provided with suitable software for processing the data received from said sensors, in order to display the static, postural and dynamic measurements of the foot-sole pressures.

2. Apparatus according to claim 1, characterized in hat it comprises moreover an external d.c. power supply (4) connected to said footboards (1*a*, 1*b*, 1*c*) via the interface board (3).

3. Apparatus according to claim 1, characterized in that said concentrator/switching module (8) consists of amplifiers (7*a*, 7*b*, 7*c*), of a number equivalent to the number of footboards (1*a*, 1*b*, 1*c*), which are connected at their input to said footboards for detecting the voltage value, and an electronic switch (10) for continuous scan-reading of the voltage from the amplifiers (7*a*, 7*b*, 7*c*).

* * * * *